United States Patent
Zhou et al.

(10) Patent No.: US 10,723,675 B2
(45) Date of Patent: Jul. 28, 2020

(54) PROCESS FOR MAKING XYLENES AND PHENOL FROM COAL DERIVED LIQUIDS

(71) Applicants: CHINA PETROLEUM & CHEMICAL CORPORATION, Beijing (CN); UOP LLC, Des Plaines, IL (US)

(72) Inventors: Lubo Zhou, Deer Park, IL (US); Shuguang Zhang, Wilmette, IL (US)

(73) Assignees: China Petroleum & Chemical Corporation, Beijing (CN); UOP LLC, Des Plaines, IL (US)

( * ) Notice: Subject to any disclaimer, the term of this patent is extended or adjusted under 35 U.S.C. 154(b) by 0 days.

(21) Appl. No.: 16/593,125

(22) Filed: Oct. 4, 2019

(65) Prior Publication Data

US 2020/0031741 A1    Jan. 30, 2020

Related U.S. Application Data

(63) Continuation of application No. PCT/US2017/062827, filed on Nov. 21, 2017.

(51) Int. Cl.
| | | |
|---|---|---|
| *C07C 6/00* | (2006.01) | |
| *C07C 15/08* | (2006.01) | |
| *C07C 37/48* | (2006.01) | |
| *C07C 39/00* | (2006.01) | |
| *C07C 6/12* | (2006.01) | |
| *C07C 39/04* | (2006.01) | |

(52) U.S. Cl.
CPC ............. *C07C 6/126* (2013.01); *C07C 15/08* (2013.01); *C07C 37/48* (2013.01); *C07C 39/04* (2013.01)

(58) Field of Classification Search
CPC ......... C07C 6/126; C07C 15/08; C07C 37/48; C07C 37/04
See application file for complete search history.

(56) References Cited

U.S. PATENT DOCUMENTS

| | | |
|---|---|---|
| 2,838,763 A | 7/1954 | Lien et al. |
| 3,284,514 A | 11/1966 | Dedinas et al. |
| 4,041,091 A | 8/1977 | Henry |
| 4,191,844 A | 3/1980 | Bjornson |
| 4,205,017 A | 5/1980 | Bjornson |
| 4,230,895 A | 10/1980 | Daly |
| 4,431,850 A | 2/1984 | Huibers et al. |
| 4,605,790 A | 8/1986 | Wojtkowski |
| 9,079,816 B2 | 7/2015 | Johnson et al. |
| 9,295,962 B2 | 3/2016 | Zheng et al. |
| 9,434,661 B2 | 9/2016 | Ou et al. |

FOREIGN PATENT DOCUMENTS

| | | |
|---|---|---|
| CN | 106187671 A | 12/2016 |
| GB | 1232027 | 5/1971 |
| WO | 2015094500 A2 | 6/2015 |
| WO | 2016012103 A1 | 1/2016 |

OTHER PUBLICATIONS

International Search Report from PCT Application No. PCT/US2017/062827, dated Feb. 22, 2018.
Written Opinion from PCT Application No. PCT/US2017/062827, dated Feb. 22, 2018.
Thakur, Ruchika, et al., Optimization of Process Parameters for Transalkylation of Toluene to Xylene using Response Surface Methodology, Particulate Science and Technology, DOI: 10.1080/02726351.2015.1081656, 2015.
Hialgeri, Anand B. et al., Recent advances in selectivation of zeolites for para-disubstituted aromatics, Catalysis Today 73 (2002), 65-73.
Zhu, Xinli, et al., Efficient Conversion of m-Cresol to Aromatics on a Bifunctional Pt/HBeta Catalyst, Energy Fuels 2014, 4104-4111.
Given, P.H., Reactions of Alkyphenols Over Cracking Catalysts. Isomeric Composition of the Products from a Series of Phenols, J. appl. Chem. 7, Apr. 1957.
Kodera, Yoichi, et al., Separation of Phenolic Compounds from Coal Liquids, National Research Institute for Pollution and Resources, Japan, 2008.

*Primary Examiner* — Sikarl A Witherspoon

(57) ABSTRACT

Processes and apparatus for making xylenes and phenol are described. Phenol and alkyl phenols are separated from coal derived liquid. The phenol is separated from the alkyl phenols. The alkyl phenols can be reacted with aromatics such as benzene and toluene to make xylenes. The xylenes and other aromatics are then separated from the phenol and alkyl phenols. Para-xylene is separated and recovered using a xylene separation process, and meta-xylene and ortho-xylene are optionally converted to para-xylene through an isomerization reaction.

20 Claims, 2 Drawing Sheets

PROCESS FOR MAKING XYLENES AND PHENOL FROM COAL DERIVED LIQUIDS

This application is a continuation of PCT/US2017/062827, entitled Process for Making Xylenes and Phenol from Coal Derived Liquids, filed Nov. 21, 2017, which is incorporated herein in its entirety.

BACKGROUND

Coal tar is one of the liquids derived from coal. Low temperature coal tar is a by-product from semi-coke generation or low temperature gasification using low rank coal (young coal), such as lignite, as feed. Coal derived liquid can also be generated from direct coal liquefaction. Liquid generated from young coal in China usually contains high level of oxygenates. It has been reported that low and mid-temperature coal tars in China contain about 20-30% phenols. The phenols in the coal derived liquid are mixture of many kinds of phenols including single ring phenols such as phenol, cresols, xylenols, longer alkyl or multi-alkyl phenols, benzenediols, and alkyl benzenediols, as well as multi-ring phenols, such as naphthols and alkyl naphthols.

Because of their extremely complicated compositions, most coal tars have been limited to being used as heating fuel, a low value application. In addition, burning coal tars without treatment has created a lot of environmental issues in many areas of China. Recently, hydroprocessing coal tars through hydrogenation to make diesel, gasoline, and other chemicals such as aromatics has become more and more popular in China. Since the concentration of phenols in coal tar is quite high, it is desirable to remove the phenols before the coal tar liquid is processed in a hydro-processing unit. Otherwise, the oxygen in the phenols will consume hydrogen (to make water) in the hydro-processing unit increasing the hydrogen consumption, which increases the cost of hydro-processing. Formation of large amount of water can also be detrimental to the hydroprocessing catalysts. Additionally, phenols generally have higher value than fuels.

Multiple technologies have been developed to recover phenols from coal tar. The traditional technology is washing the coal tar liquid with a base followed by an acid neutralization to recover phenols because phenols are acidic. The phenols are easily recovered, but separating them to obtain individual pure products is difficult. In addition, although there is a demand for phenol itself, the demand for alkyl phenols is quite low.

Therefore, there is a need for a process for treating coal derived liquids to recover and process phenols from the coal derived liquids.

DETAILED DESCRIPTION

Figure 1:
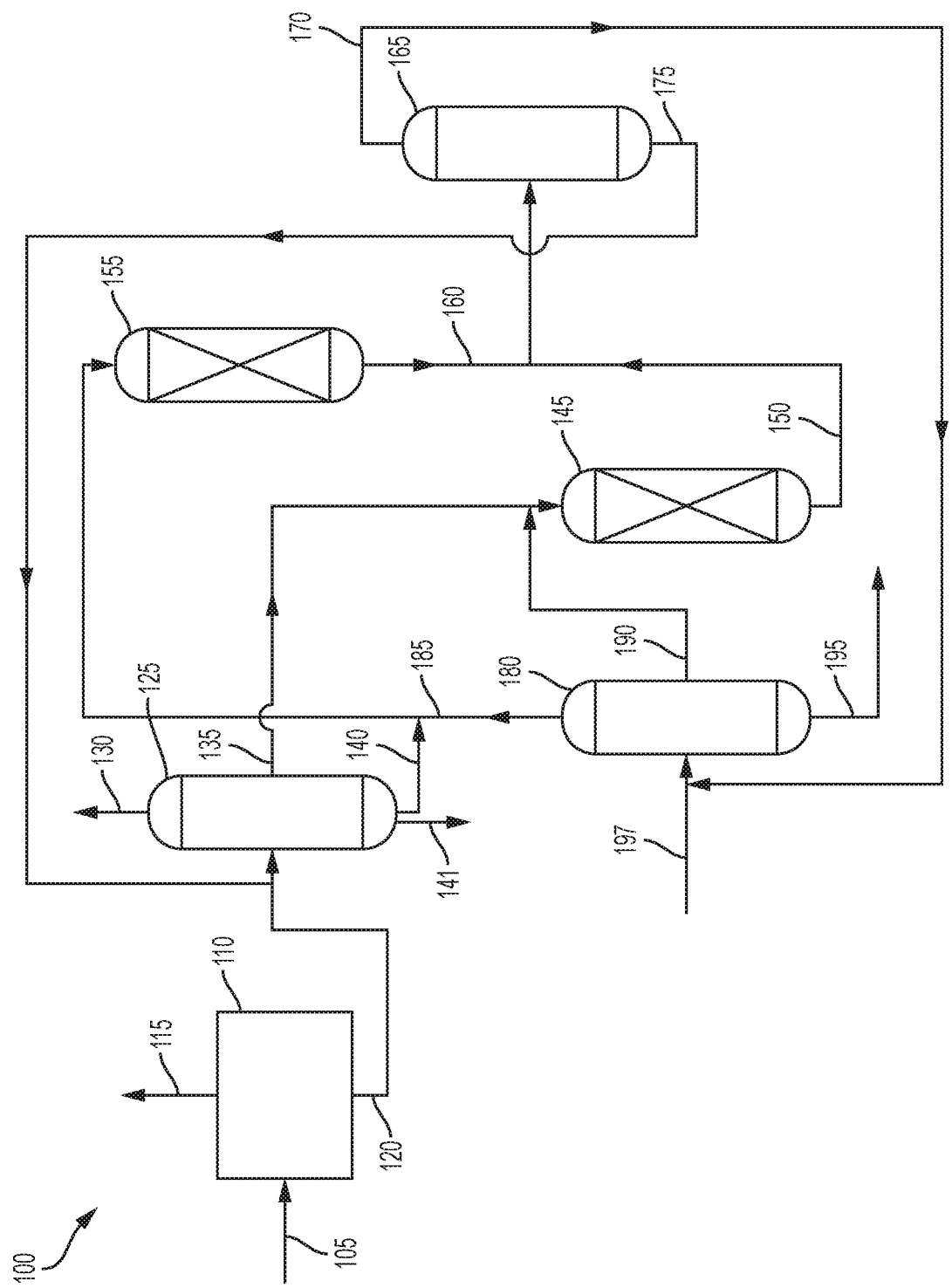
FIG. 1 is an illustration of one embodiment of the process of the present invention.

Xylenes and phenol are very important chemicals, and there is a strong demand for them world-wide. Xylenes are often utilized in the production of polymers, which are widely used in everyday life. For example, para-xylene is the basic chemical used to make polyester fiber and resin. Phenol can be used to make polycarbonate, epoxide, phenolic resins, and cyclohexane, the basic chemical used to make nylon.

One aspect of the invention involves a process that can separate phenols from the coal derived liquid. The phenols can then be recovered and/or converted to high value products including para-xylene and phenol. In one embodiment, phenol and alkyl phenols are separated and recovered from coal derived liquid. Phenol can be then separated from alkyl phenols. The alkyl phenols can be reacted with aromatics such as benzene and toluene to make xylenes. In some embodiments, meta-xylene and ortho-xylene can be converted to para-xylene through an isomerization reaction, and the para-xylene can be separated and recovered using a xylenes separation process.

The process involves transalkylation between alkyl phenols and aromatics. Transalkylation is a chemical reaction resulting in transfer of one or more of the alkyl groups from the alkyl phenols to the aromatics.

Another aspect of the invention is an apparatus making xylenes and phenol. In one embodiment, the apparatus includes a phenols separation zone having an inlet, a phenol product outlet, a cresols outlet, and a xylenols outlet; a cresols transalkylation reaction zone having an inlet, and an outlet, the cresols transalkylation reaction zone inlet being in fluid communication with the cresols outlet; a xylenols transalkylation reaction zone having an inlet, and an outlet, the xylenols transalkylation reaction zone inlet being in fluid communication with the xylenols outlet; a phenols and aromatics separation zone having an inlet, an aromatics outlet, and a phenols outlet, the phenols and aromatics separation zone inlet being in fluid communication with the cresols transalkylation reaction zone outlet and the xylenols transalkylation reaction zone outlet, the phenols outlet being in fluid communication with the phenols separation zone inlet; an aromatics separation zone having an inlet, a benzene outlet, a toluene outlet, and a xylenes outlet, the aromatics separation zone inlet being in fluid communication with the aromatics outlet, the benzene outlet being in fluid communication with the xylenols transalkylation reaction zone inlet, and the toluene outlet being in fluid communication with the cresols transalkylation reaction zone inlet. Optionally, the apparatus can include a xylenes separation zone having a first inlet, a second inlet, a para-xylene outlet, and a xylenes outlet, the xylenes separation zone first inlet being in fluid communication with the aromatics separation zone xylenes outlet; and a xylenes isomerization zone having an inlet and an outlet, the xylenes isomerization zone inlet being in fluid communication with the xylenes separation zone xylenes outlet, the xylenes isomerization zone outlet being in fluid communication with the xylenes separation zone second inlet.

FIG. 1 illustrates one embodiment of the process 100. In the process 100, coal tar 105 is fed to a coal tar separation zone 110, where it is separated into a hydrocarbon stream 115 and a first phenols stream 120. The hydrocarbon stream 115 contains hydrocarbons such as paraffins, cycloparaffins, olefins, and aromatics. The first phenols stream 120 contains phenol and alkyl phenols.

The coal tar separation zone can be any suitable zone for separating coal tar. Suitable separation processes include, but are not limited to, distillation, acid and caustic extraction, solvent extraction, adsorption with adsorbent, membrane separation, supercritical fluid extraction, crystallization, chelation, and eutectic reaction, and combinations thereof.

The first phenols stream 120 is sent to a phenols separation zone 125 where it is separated into at least two streams. As shown, the first phenols stream 120 is separated into a phenol product stream 130, a cresols stream 135, a xylenols stream 140, and a higher phenols stream 141. The phenol product stream 130 comprises phenol, which can be recovered as the phenol product. The cresols stream 135 comprises cresols of various types. The xylenols stream 140 comprises various xylenols. The higher phenols stream 141 contains phenols that are heavier than xylenols, such as propylphenols, butylphenols and naphthols.

The phenols separation zone 125 can be any suitable separation zone for separating phenols, cresols, xylenols, and higher phenols. Suitable processes include, but are not limited to, distillation, adsorption, extraction, crystallization, and combinations thereof.

The cresols stream 135 is sent to cresols transalkylation reaction zone 145 where the cresols are reacted with toluene and/or benzene. The toluene and/or benzene can be mixed with the cresols stream 135 before entering the cresols transalkylation reaction zone 145, or they can be added separately, Any suitable cresols transalkylation catalyst can be used. The cresols transalkylation catalyst is typically selected to have relatively high stability at a high activity level. Suitable cresols transalkylation catalysts include, but are not limited to, homogeneous acid catalysts, such as mineral acids, or heterogeneous acid catalysts such as zeolites, acidic resins, heteropoly acids, amorphous silica alumina, mixed oxides, like tungstated zirconia and sulfated zirconia, and the like, and combinations thereof.

The cresols and toluene and/or benzene are usually heated to reaction temperature and then passed through the cresols transalkylation reaction zone 145, which may comprise one or more individual reactors. Passage of the combined feed through the cresols transalkylation reaction zone 145 produces a first effluent stream 150 comprising aromatics, phenol, and alkyl phenols.

The cresols transalkylation reaction can be effected in contact with a catalytic composite in any conventional or otherwise convenient manner and may comprise a batch or continuous type of operation, with a continuous operation being preferred. The cresols transalkylation catalyst is usefully disposed in various types of reaction zones, including, but not limited to, fixed bed reaction zones, moving bed reaction zones, and fluidized bed reaction zones.

The cresols transalkylation reaction zone 145 normally operates at reaction conditions including a temperature in the range of 50° C. to 600° C., or 100° C. to 500° C. The cresols transalkylation reaction zone 145 is typically operated at moderately elevated pressures broadly ranging from 0 MPa to 7.6 MPa gauge, or 0.01 MPa to 5 MPa gauge. The cresols transalkylation reaction can be effected over a wide range of liquid hourly space velocities (LHSV). The LHSV is generally in the range of from 0.1 to 5 $hr^{-1}$, or 0.2 to 4 $hr^{-1}$. In some embodiments, the cresols transalkylation reaction takes place under reactions conditions comprising a temperature in a range of 50° C. to 600° C.; a pressure in a range of 0 MPa(g) to 7.6 MPa(g); and a LHSV in a range of 0.1 to 5 $hr^{-1}$. In some embodiments, the cresols transalkylation reaction takes place under reactions conditions comprising a temperature in a range of 100° C. to 500° C.; a pressure in a range of 0.01 MPa(g) to 5 MPa(g); and a LHSV in a range of 0.2 to 4 $hr^{-1}$.

Optionally, a gas, including, but not limited to, hydrogen, steam or nitrogen, may be added to the cresols transalkylation reaction zone 145 to prevent coke formation or to remove coke.

The xylenols stream 140 is sent to xylenols transalkylation reaction zone 155 where the xylenols are reacted with benzene and/or toluene. The toluene and/or benzene can be mixed with the xylenols stream 140 before entering the xylenols transalkylation reaction zone 155, or they can be added separately, Any suitable xylenols transalkylation catalyst can be used. The catalyst is typically selected to have relatively high stability at a high activity level. Suitable xylenols transalkylation catalysts are those listed above for cresols.

The xylenols and benzene and/or toluene are heated to reaction temperature and then passed through the xylenols transalkylation reaction zone 155, which may comprise one or more individual reactors. Passage of the combined feed through the xylenols transalkylation reaction zone 155 produces a second effluent stream 160 comprising aromatics, phenol, and alkyl phenols.

The xylenols transalkylation reaction can be effected in contact with a catalytic composite in any conventional or otherwise convenient manner and may comprise a batch or continuous type of operation, with a continuous operation being preferred. The xylenols transalkylation catalyst is usefully disposed in various types of reaction zones, including, but not limited to, fixed bed reaction zones, moving bed reaction zones, and fluidized bed reaction zones.

The xylenols transalkylation reaction zone 155 normally operates at reaction conditions including a temperature in the range of 50° C. to 600° C., or 100° C. to 500° C. The transalkylation zone is typically operated at moderately elevated pressures broadly ranging from 0 MPa to 7.6 MPa gauge, or 0.01 MPa to 5 MPa gauge. The transalkylation reaction can be effected over a wide range of liquid hourly space velocities (LHSV). The LHSV is generally in the range of from 0.1 to 5 $hr^{-1}$, or 0.2 to 4 $hr^{-1}$. In some embodiments, the xylenols transalkylation reaction takes place under reactions conditions comprising a temperature in a range of 50° C. to 600° C.; a pressure in a range of 0 MPa(g) to 7.6 MPa(g); and a LHSV in a range of 0.1 to 5 $hr^{-1}$. In some embodiments, the xylenols transalkylation reaction takes place under reactions conditions comprising a temperature in a range of 100° C. to 500° C.; a pressure in a range of 0.01 MPa(g) to 5 MPa(g); and a LHSV in a range of 0.2 to 4 $hr^{-1}$.

Optionally, a gas, including, but not limited to, hydrogen, steam or nitrogen, may be added to the xylenols transalkylation reaction zone 155 prevent coke formation or to remove coke.

The first effluent stream 150 from the cresols transalkylation reaction zone 145 and the second effluent stream 160 from the xylenols transalkylation reaction zone 155 are sent to phenols and aromatics separation zone 165 where they are separated into aromatics stream 170 and second phenols stream 175. The first effluent stream 150 and the second effluent stream 160 can be combined before being introduced into the phenols and aromatics separation zone 165, or they can be introduced separately. Phenols and aromatics separation zone 165 can involve any process for separating phenol and alkyl phenols from other aromatics, including, but not limited to, distillation, acid and caustic extraction, solvent extraction, adsorption with adsorbent, membrane separation, supercritical fluid extraction, crystallization, chelation, and eutectic reaction, or combinations thereof.

Aromatics stream 170 comprises aromatics including benzene, toluene, and xylenes, and possibly heavier aromatics. Second phenols stream 175 comprises phenol and alkyl phenols.

Aromatics stream 170 is sent to aromatics separation zone 180 where it is separated into a benzene stream 185 comprising benzene, a toluene stream 190 comprising toluene, and a xylenes stream 195 comprising one or more of para-xylene, meta-xylene, and ortho-xylene and possibly some heavier aromatics. Alternatively, there could be a stream comprising benzene and toluene. The toluene stream 190 provides the toluene for reaction with the cresols in the cresols transalkylation reaction zone 145, while the benzene stream 185 provides benzene for the reaction with the xylenols in the xylenols transalkylation reaction zone 155. The xylenes stream 195 can be recovered and sent for further processing.

The aromatics separation zone 180 can involve any suitable process for separating xylenes from benzene and/or toluene. Suitable aromatics separation processes include, but are not limited to, distillation, adsorption with adsorbent, crystallization, membrane separation, supercritical fluid extraction, and combinations thereof.

In some embodiments, a feed stream 197 of aromatics can be fed into the aromatics separation zone 180.

The second phenols stream 175 is sent to the phenols separation zone 125 where the phenol is separated from the alkyl phenols. The second phenols stream 175 can be mixed with the first phenols stream 120 before being introduced into the phenols separation zone 125, or they can be added separately.

Figure 2:
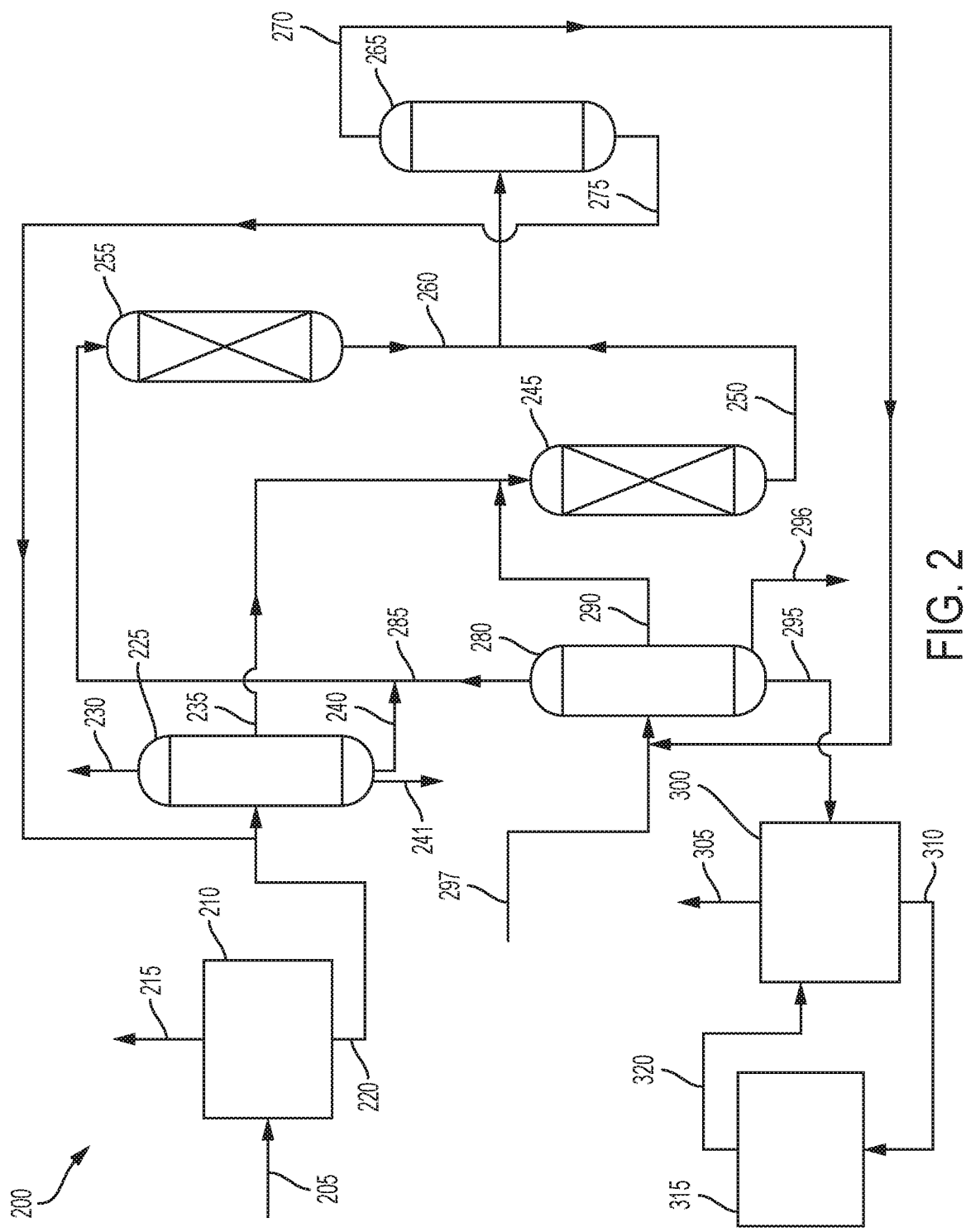
FIG. 2 is an illustration of another embodiment of the process of the present invention.

FIG. 2 illustrates another embodiment of the process 200, which is generally similar to process 100. Coal tar 205 is fed to a coal tar separation zone 210, where it is separated into a hydrocarbon stream 215 and a first phenols stream 220.

The first phenols stream 220 is sent to a phenols separation zone 225 where it is separated into at least two streams. As shown, the first phenols stream 220 is separated into a phenol product stream 230, a cresols stream 235, a xylenols stream 240, and a higher phenols stream 241.

The cresols stream 235 is sent to cresols transalkylation reaction zone 245 where the cresols are reacted with toluene and/or benzene. The toluene and/or benzene can be mixed with the cresols stream 235 before entering the cresols transalkylation reaction zone 245, or they can be added separately. Effluent stream 250 comprising aromatics, phenol, and alkyl phenols.

The xylenols stream 240 is sent to xylenols transalkylation reaction zone 255 where the xylenols are reacted with benzene and/or toluene. The toluene and/or benzene can be mixed with the xylenols stream 240 before entering the xylenols transalkylation reaction zone 255, or they can be added separately. Effluent stream 260 comprising aromatics, phenol, and alkyl phenols.

The effluent stream 250 from the cresols transalkylation reaction zone 245 and the effluent stream 260 from the xylenols transalkylation reaction zone 255 are sent to phenols and aromatics separation zone 265 where they are separated into aromatics stream 270 and second phenols stream 275. The first effluent stream 250 and the second effluent stream 260 can be combined before being introduced into the phenols and aromatics separation zone 265, or they can be introduced separately.

Aromatics stream 270 is sent to aromatics separation zone 280 where it is separated into a benzene stream 285, a toluene stream 290, a first xylenes stream 295, and a heavier aromatics stream 296. Alternatively, there could be a stream comprising benzene and toluene. The toluene stream 290 provides the toluene for reaction with the cresols in the cresols transalkylation reaction zone 245, while the benzene stream 285 provides benzene for the reaction with the xylenols in the xylenols transalkylation reaction zone 255.

In some embodiments, a feed stream 297 of aromatics can be fed into the aromatics separation zone 280.

The second phenols stream 275 is sent to the phenols separation zone 225 where the phenol is separated from the alkyl phenols. The second phenols stream 275 can be mixed with the first phenols stream 220 before being introduced into the phenols separation zone 225, or they can be added separately.

The first xylenes stream 295 is sent to xylenes separation zone 300 where it is separated into para-xylene product stream 305 comprising para-xylene and second xylenes stream 310 comprising ortho-xylene and meta-xylene.

Any suitable xylenes separation process can be used, including but not limited to, distillation, adsorption (for example, UOP's Parex™ process), crystallization (for example, BP/CBI's pX process), or combinations of these processes.

The second xylenes stream 310 is sent to a xylenes isomerization reaction zone 315 where it is isomerized in the presence of a xylenes isomerization catalyst. Suitable xylenes isomerization processes include, but are not limited to, UOP's Isomar™ process. The isomerized xylenes stream 320 is sent to xylenes separation zone 300 for separation. The xylenes isomerization reaction zone 315 normally operates at reaction conditions including a temperature in the range of 50° C. to 600° C., or 100° C. to 500° C. The xylenes isomerization zone 315 is typically operated at moderately elevated pressures broadly ranging from 0 MPa to 7.6 MPa gauge, or 0.01 MPa to 5 MPa gauge. The xylenes isomerization reaction can be effected over a wide range of liquid hourly space velocities (LHSV). The LHSV is generally in the range of from 0.1 to 5 $hr^{-1}$, or 0.2 to 4 $hr^{-1}$. In some embodiments, the xylenes isomerization reaction takes place under reactions conditions comprising a temperature in a range of 50° C. to 600° C.; a pressure in a range of 0 MPa(g) to 7.6 MPa(g); and a LHSV in a range of 0.1 to 5 $hr^{-1}$. In some embodiments, the xylenes isomerization reaction takes place under reactions conditions comprising a temperature in a range of 100° C. to 500° C.; a pressure in a range of 0.01 MPa(g) to 5 MPa(g)); and a LHSV in a range of 0.2 to 4 $hr^{-1}$.

Optionally, a gas, including, but not limited to, hydrogen, steam or nitrogen, may be added to the xylenes isomerization reaction zone 315 prevent coke formation or to remove coke.

Any suitable xylenes isomerization catalyst can be used. Suitable xylenes isomerization catalysts include, but are not limited to, both homogeneous catalysts, such as BF3-HF, and heterogeneous catalysts, such as amorphous silica alumina, zeolites or metal promoted zeolites. The catalyst is typically selected to have relatively high stability at a high activity level.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for making xylenes and phenol comprising:
providing a first phenols stream comprising phenol and alkyl phenols from a coal derived liquid;
separating the first phenols stream into at least a phenol product stream comprising phenol, and a cresols stream comprising cresols in a phenols separation zone;
transalkylating the cresols stream with a first aromatics stream comprising toluene, benzene, or both in a cresols transalkylation reaction zone in the presence of a cresols transalkylating catalyst to form a first effluent stream comprising aromatics, phenol, and alkyl phenols;
separating the first effluent stream into at least a second aromatics stream comprising aromatics and a second phenols stream comprising phenol and alkyl phenols in a phenols and aromatics separation zone;
separating the second aromatics stream into at least the first aromatics stream and a first xylenes stream comprising para-xylene, ortho-xylene, and meta-xylene in an aromatics separation zone; and
introducing the second phenols stream into the phenols separation zone.

2. The process of claim 1 wherein separating the first phenols stream into at least the phenol product stream, and the cresols stream comprises separating the first phenols stream into at least the phenol product stream, the cresols stream, and a xylenols stream comprising xylenols; wherein the first aromatics stream comprises toluene; and wherein separating the second aromatics stream into at least the first aromatics stream and the first xylenes stream comprises separating the second aromatics stream into at least the toluene stream, the first xylenes stream, and a benzene stream comprising benzene; and further comprising:
transalkylating the xylenols stream with the benzene stream in a xylenols transalkylation reaction zone in the presence of a xylenols transalkylation catalyst to form a second effluent stream comprising aromatics, phenol, and alkyl phenols;
combining the first effluent stream and the second effluent stream to form a combined stream; and
wherein separating the first effluent stream into at least the second aromatics stream and the second phenols stream comprises separating the combined stream into at least the second aromatics stream and the second phenols stream.

3. The process of claim 2 further comprising separating the first xylenes stream into a para-xylene product stream comprising para-xylene and a second xylenes stream comprising ortho-xylene and meta-xylene in a xylenes separation zone.

4. The process of claim 3 further comprising:
isomerizing the second xylenes stream in a xylenes isomerization zone in the presence of a xylenes isomerization catalyst to form an isomerized xylenes stream comprising para-xylene, ortho-xylene, and meta-xylene; and
introducing the isomerized xylenes stream into the xylenes separation zone.

5. The process of claim 1 further comprising introducing a feed stream comprising aromatics to the aromatics separation zone.

6. The process of claim 1 wherein providing a first phenols stream comprises separating the phenols from the coal derived liquid using distillation, acid and caustic extraction, solvent extraction, adsorption with adsorbent, membrane separation, supercritical fluid extraction, crystallization, chelation, and eutectic reaction, and combinations thereof.

7. The process of claim 1 wherein transalkylating the cresols stream with the first aromatics stream takes place under reaction conditions comprising at least one of: a temperature in a range of 50° C. to 600° C.; a pressure in a range of 0 MPa(g) to 7.6 MPa(g); and a LHSV in a range of 0.1 to 5 $hr^{-1}$.

8. The process of claim 2 wherein transalkylating the xylenols stream with the benzene stream takes place under reaction conditions comprising at least one of: a temperature in a range of 50° C. to 600° C.; a pressure in a range of 0 MPa(g) to 7.6 MPa(g); and a LHSV in a range of 0.1 to 5 $hr^{-1}$.

9. The process of claim 4 wherein isomerizing the second xylenes stream takes place under reactions conditions comprising at least one of: a temperature in a range of 50° C. to 600° C.; a pressure in a range of 0 MPa(g) to 7.6 MPa(g); and a LHSV in a range of 0.1 to 5 $hr^{-1}$.

10. The process of claim 1 wherein the cresols transalkylation catalyst comprises at least one homogeneous acid catalyst, or at least one a heterogeneous acid catalyst.

11. A process for making xylenes and phenol comprising:
providing a first phenols stream comprising phenol and alkyl phenols from a coal derived liquid;
separating the first phenols stream into at least a phenol product stream comprising phenol, a cresols stream comprising cresols, and a xylenols stream comprising xylenols in a phenols separation zone;
transalkylating the cresols stream with a toluene stream comprising toluene in a cresols transalkylation reaction zone in the presence of a cresols transalkylating catalyst to form a first effluent stream comprising aromatics, phenol, and alkyl phenols;
transalkylating the xylenols stream with a benzene stream comprising benzene in a xylenols transalkylation reaction zone in the presence of a xylenols transalkylating catalyst to form a second effluent stream comprising aromatics, phenol, and alkyl phenols;
separating the first effluent stream and the second effluent stream into at least an aromatics stream comprising aromatics and a second phenols stream comprising phenol and alkyl phenols in a phenols and aromatics separation zone;
separating the aromatics stream into at least the benzene stream, the toluene stream, and a first xylenes stream comprising para-xylene, ortho-xylene, and meta-xylene in an aromatics separation zone; and
introducing the second phenols stream into the phenols separation zone.

12. The process of claim 11 further comprising separating the first xylenes stream into a para-xylene product stream comprising para-xylene and a second xylenes stream comprising ortho-xylene and meta-xylene in a xylenes separation zone.

13. The process of claim 12 further comprising:
isomerizing the second xylenes stream in a xylenes isomerization zone in the presence of a xylenes isomerization catalyst to form an isomerized xylenes stream comprising para-xylene, ortho-xylene, and meta-xylene; and
introducing the isomerized xylenes stream into the xylenes separation zone.

14. The process of claim 11 further comprising introducing a feed stream comprising aromatics to the aromatics separation zone.

15. The process of claim 11 wherein providing phenols from the coal derived liquid comprises separating the phenols from the coal derived liquid using distillation, acid and caustic extraction, solvent extraction, adsorption with adsorbent, membrane separation, supercritical fluid extraction, crystallization, chelation, and eutectic reaction, and combinations thereof.

16. The process of claim 11 wherein transalkylating the cresols stream with the toluene stream takes place under reactions conditions comprising at least one of: a temperature in a range of 50° C. to 600° C.; a pressure in a range of 0 MPa(g) to 7.6 MPa(g); and a LHSV in a range of 0.1 to 5 hr$^{-1}$.

17. The process of claim 11 wherein transalkylating the xylenols stream with the benzene stream takes place under reactions conditions comprising at least one of: a temperature in a range of 50° C. to 600° C.; a pressure in a range of 0 MPa(g) to 7.6 MPa(g); and a LHSV in a range of 0.1 to 5 hr$^{-1}$.

18. The process of claim 13 wherein isomerizing the second xylenes stream takes place under reactions conditions comprising at least one of: a temperature in a range of 50° C. to 600° C.; a pressure in a range of 0 MPa(g) to 7.6 MPa(g); and a LHSV in a range of 0.1 to 5 hr$^{-1}$.

19. The process of claim 11 wherein at least one of the cresols transalkylation catalyst and the xylenols transalkylation catalyst comprises at least one homogeneous acid catalyst, or at least one heterogeneous acid catalyst.

20. A process for making para-xylene and phenol comprising:
providing a first phenols stream comprising phenol and alkyl phenols from a coal derived liquid;
separating the first phenols stream into at least a phenol product stream comprising phenol, a cresols stream comprising cresols, and a xylenols stream comprising xylenols in a phenols separation zone;
transalkylating the cresols stream with a toluene stream comprising toluene in a cresols transalkylation reaction zone in the presence of a cresols transalkylating catalyst to form a first effluent stream comprising aromatics, phenol, and alkyl phenols;
transalkylating the xylenols stream with a benzene stream comprising benzene in a xylenols transalkylation reaction zone in the presence of a xylenols transalkylating catalyst to form a second effluent stream comprising aromatics, phenol, and alkyl phenols;
separating the first effluent stream and the second effluent stream into at least an aromatics stream comprising aromatics and a second phenols stream comprising phenol and alkyl phenols in a phenol and aromatics separation zone;
separating the aromatics stream into at least the benzene stream, the toluene stream, and a first xylenes stream comprising para-xylene, ortho-xylene, and meta-xylene in an aromatics separation zone;
introducing the second phenols stream into the phenol separation zone;
separating the first xylenes stream into a para-xylene product stream comprising para-xylene and a second xylenes stream comprising ortho-xylene and meta-xylene in a xylenes separation zone;
isomerizing the second xylenes stream in a xylenes isomerization zone in the presence of a xylenes isomerization catalyst to form an isomerized xylenes stream comprising para-xylene, ortho-xylene, and meta-xylene; and
introducing the isomerized xylenes stream into the xylenes separation zone.

* * * * *